United States Patent [19]

Ohta et al.

[11] Patent Number: 5,234,665
[45] Date of Patent: Aug. 10, 1993

[54] APPARATUS FOR MEASURING AGGREGATION PATTERNS ON A MICROPLATE

[75] Inventors: Masato Ohta, Kawasaki; Yasuhiko Yokomori, Yokohama; Toshiyuki Furuta, Yokohama; Hideo Suda, Yokohama; Naoki Ozawa; Shogo Kida, both of Kawasaki, all of Japan

[73] Assignee: Suzuki Motor Corporation, Shizuoka, Japan

[21] Appl. No.: 700,567

[22] Filed: May 15, 1991

[30] Foreign Application Priority Data

May 25, 1990 [JP] Japan .................................. 2-136020

[51] Int. Cl.⁵ .................. G01N 33/50; G06K 9/32; G06K 9/74
[52] U.S. Cl. ................................. 422/73; 422/65; 422/67; 422/82.05; 356/244; 356/442; 382/6
[58] Field of Search ................ 382/6, 65; 356/244, 356/442; 422/65, 67, 73, 82.05

[56] References Cited

U.S. PATENT DOCUMENTS

| | | | |
|---|---|---|---|
| 4,318,886 | 3/1982 | Kawahara et al. | 422/82.05 |
| 4,452,759 | 6/1984 | Takekawa | 356/442 X |
| 4,563,430 | 1/1986 | Kano et al. | 422/73 X |
| 4,580,895 | 4/1986 | Patel | 422/73 X |
| 4,727,033 | 2/1988 | Hijikata et al. | 422/73 X |
| 4,730,921 | 3/1988 | Klein et al. | 422/73 X |
| 4,794,450 | 12/1988 | Saito et al. | 382/6 X |
| 5,096,835 | 3/1992 | Yokomori et al. | 436/165 |

FOREIGN PATENT DOCUMENTS

63-150916 6/1988 Japan .
2-208541 8/1990 Japan .

Primary Examiner—James C. Housel
Assistant Examiner—Arlen Soderquist
Attorney, Agent, or Firm—Flynn, Thiel, Boutell & Tanis

[57] ABSTRACT

An aggregation pattern detecting apparatus includes a microplate having a plurality of reactive vessels in which aggregation patterns are formed, a light source arranged above the microplate, and a light sensor arrangement positioned below the microplate. The microplate is removably fastened to a main body, and a movable frame is movably supported on the main body. The light source and light sensor arrangement are carried on the movable frame for movement therewith. A driving mechanism effects movement of the movable frame and is controlled by a main control section. A reference plate is provided separately from the microplate, and has a plurality of through holes therein which correspond to the reactive vessels of the microplate. The reference plate is removably fastenable to the main body at the normal operative position of the microplate. With the reference plate in this position, the distance from a starting point of the driving mechanism to the through holes of the reference plate is measured and stored in the main control section. Based on these stored distances, the main control section determines appropriate operational positions for the light sensor.

6 Claims, 5 Drawing Sheets

[NON-AGGREGATION (NEGATIVE)]

FIG. 5(b) PRIOR ART

[AGGREGATION (POSITIVE)]

APPARATUS FOR MEASURING AGGREGATION PATTERNS ON A MICROPLATE

FIELD OF THE INVENTION

The present invention relates to an aggregation pattern detecting apparatus and, more particularly, to an aggregation pattern detecting apparatus comprising optical means for automatically measuring a plurality of aggregation patterns on a microplate having a plurality of reactive vessel portions, particularly, on a microplate which includes objects to be measured, a CCD line sensor, a driving apparatus thereof, and the like.

BACKGROUND OF THE INVENTION

In the medical field, hitherto, there has widely been used a method whereby aggregation patterns of blood particles, latex particles, carbon particles, and the like are discriminated and various components (for instance, a blood type, various antibodies, various proteins, and the like) in the blood, viruses, and the like are detected and analyzed. As such a discriminating method of the aggregation patterns, the microtiter method is relatively frequently used.

Figure 5A:
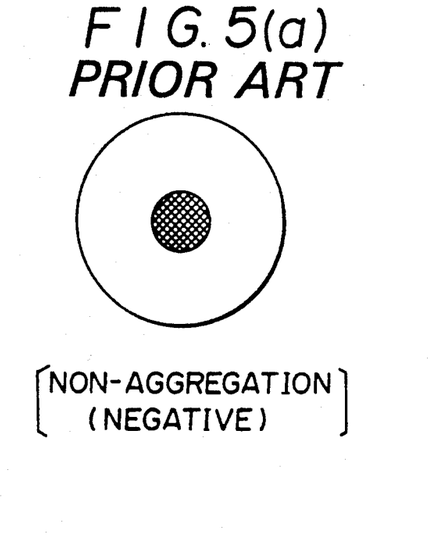
FIGS. 5(a) and 5(b) are explanatory diagrams showing examples of aggregation patterns.
Figure 5B:
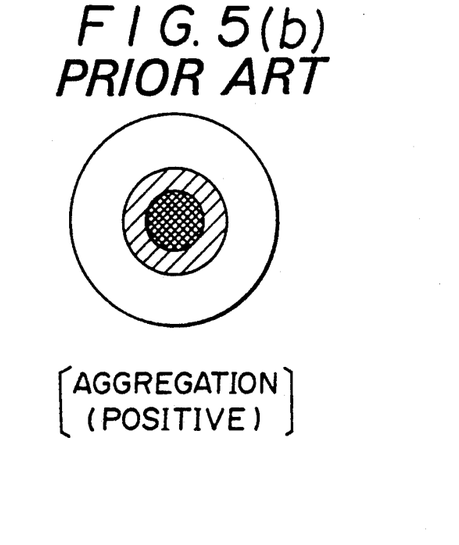

In the discrimination regarding the aggregation patterns, the presence or absence of aggregation is synthetically discriminated by a method whereby a distribution of particles in a well (i.e. reactive vessel) is detected as an area of the portions whose luminances are equal to or less than a predetermined luminance or is compared with a standard pattern or a standard non-aggregation pattern or, further, a method whereby a continuous step dilution series of a specimen sample is formed, or the like. For instance, a shadow of FIG. 5(a) is determined to be negative and a shadow of FIG. 5(b) is decided to be positive.

Figure 6:
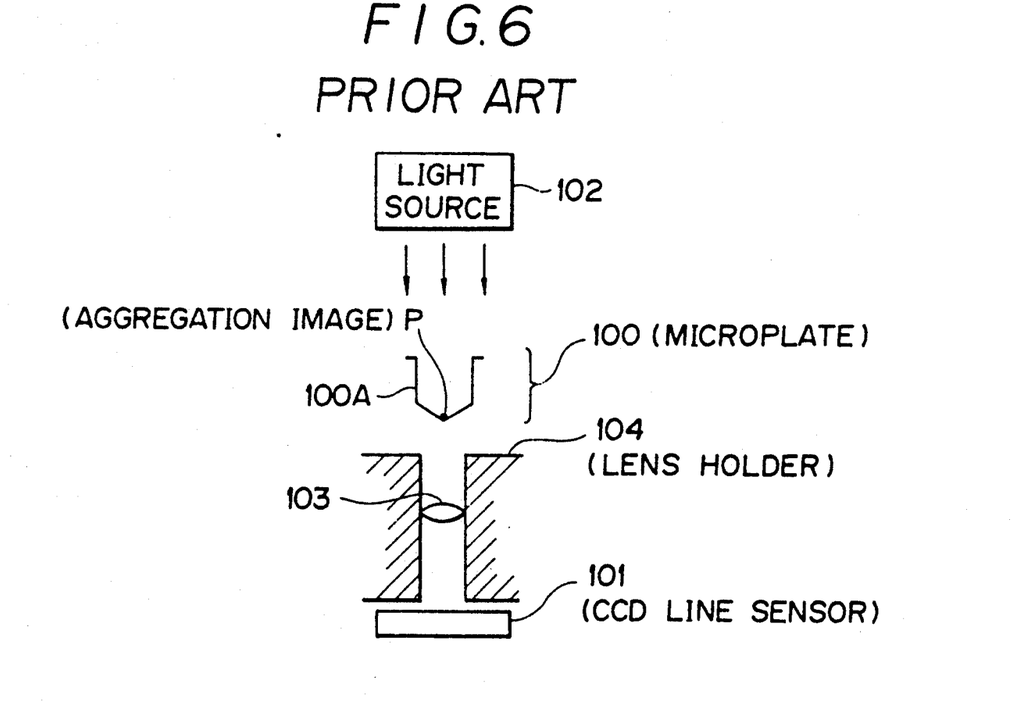
FIG. 6 is an explanatory diagram showing a conventional example.

FIG. 6 shows a conventional example wherein an aggregation pattern P in a well (reactive vessel) 100A formed on a microplate 100 is optically projected onto a CCD line sensor 101. Either line sensor 101 or microplate 100 is sequentially finely moved relative to the other in a direction perpendicular to the paper surface, thereby obtaining a (light and dark) two-dimensional image of the aggregation pattern P. In FIG. 6, reference numeral 102 denotes a light source, 103 indicates an image forming lens, and 104 a lens holder.

Figure 7:
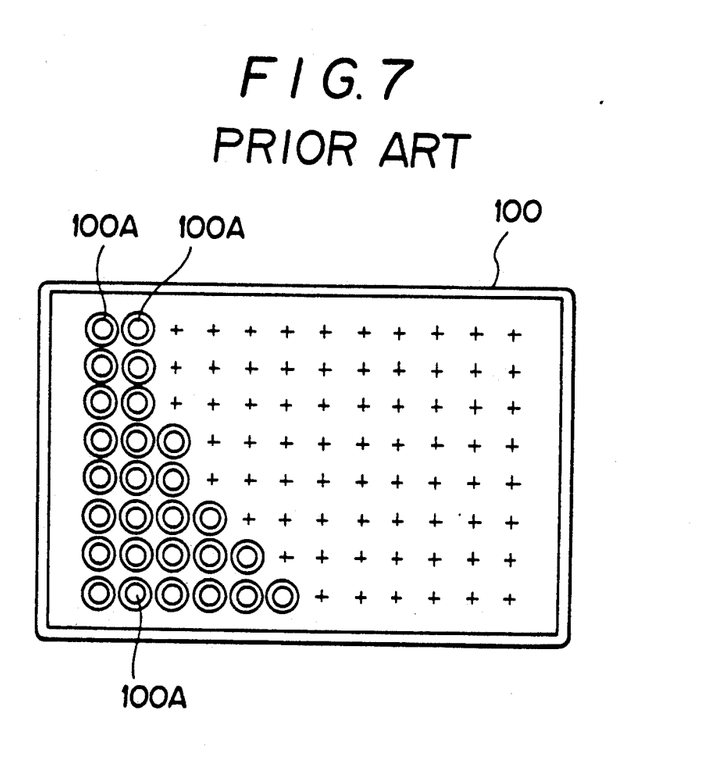
FIG. 7 is an explanatory diagram showing a conventional microplate.

On the other hand, an actual microplate 100 having a plurality of concave reactive vessel portions (wells) 100A is shown in FIG. 7. For instance, a positive or negative aggregation pattern as shown in FIG. 5 is produced in each of the wells due to the antigen and antibody reaction between the components in the blood and the reagent.

However, when setting the microplate into the apparatus main body, the setting position is mechanically preset. Therefore, if a deformation of a frame body of the apparatus main body, or a positional deviation of a movement start position (origin) of driving means for moving the photosensitive means or the like occurs, there occurs an inaccuracy in that the position of a scan start point of the CCD line sensor for the aggregation pattern is deviated. Since such a positional deviation of the scan start point of the CCD line sensor is not constant in every device produced, if such a state is left for a long time, the reliability of the measurement data deteriorates.

It is thus an object of the invention to improve upon the conventional example mentioned above and to provide an aggregation pattern detecting apparatus which can immediately set a measurement starting position for an aggregation pattern, thereby improving the reliability of the whole apparatus.

The invention comprises a microplate having a plurality of reactive vessel portions in which aggregation patterns are formed, a light source arranged above the microplate, and photosensitive means which is arranged below the microplate and has a CCD (charge coupled device) line sensor. The invention also comprises: an apparatus main body to fix the microplate; a moving frame body which is movably supported on the apparatus main body and integratedly moves the light source and the photosensitive means in a predetermined direction; driving means for intermittently or continuously setting a moving amount of the moving frame body; and a main control section to control the operation of the driving means. A reference plate having a plurality of through holes corresponding to the reactive vessels on the microplate is provided separately from the microplate. The reference plate is arranged at the attaching position of the microplate, and thereafter distances $S_0$ from a start point of the driving means to the through holes of the reference plate are measured and stored into the main control section. On the basis of the stored distances $S_0$, the main control section executes predetermined arithmetic operations and detects measurement starting positions for the reactive vessel portions on the microplate by the driving means and determines operation start timings of the CCD sensor. With the above construction, the above object is accomplished.

BRIEF DESCRIPTION OF THE DRAWINGS

An embodiment of the invention will be described hereinbelow on the basis of the drawings, in which.

DETAILED DESCRIPTION

An embodiment shown in FIGS. 1 and 2 comprises: the microplate 100 having a plurality of reactive vessel portions 100A in which aggregation patterns are formed; the light source 102 arranged above the microplate 100; and photosensitive means 90 which is arranged below the microplate 100 and has a lens system 90A and the CCD line sensor 101. Further, the embodiment comprises: an apparatus main body 91 to fixedly support the microplate 100; a moving frame body 92 which is movably supported on the apparatus main body 91 and which integratedly moves the light source 102 and the photosensitive means 90 in a predetermined direction; driving means 93 for intermittently or continuously effecting movement of the moving frame body 92; and a main control section 1 to control the operation of the driving means 93.

The microplate 100 is removably fastened to the main body 91 using any conventional means such as threaded fasteners extending through the corner portions of the microplate 100 and into the main body 91, or conventional releasable clamping devices which clamp the microplate downwardly onto the main body 91. Of course, other conventional fastening arrangements can be used.

A reference plate 2 (FIG. 3) having a plurality of through holes 2A corresponding to the reactive vessels 100A on the microplate 100 is provided separately from the microplate 100. The reference plate is used to store predetermined distance data $S_0$ (FIG. 4) into the main control section 1 and is not used when aggregation patterns are measured. The reference plate 2 is removably arranged on the main body 91 at the mechanically preset attaching position of the microplate 100 after determining that the microplate is not positioned at the preset position on the support surface of main body 91. The reference plate removably fastened to the main body 91 using the same conventional means as discussed above relative to the microplate 100. After that, the reference plate 2 is used to measure the distances $S_0$ from the start point (origin) of the driving means 93 to the through holes 2A of the reference plate 2 and to store the distances $S_0$ into the main control section 1. On the basis of the stored distances $S_0$, the main control section 1 executes predetermined arithmetic operations and determines measurement starting positions for the reactive vessel portions 100A on the microplate 100 by the driving means 93 and sets operation start timings of the CCD line sensor 101 and, thereafter, controls the whole operation.

Figure 1:
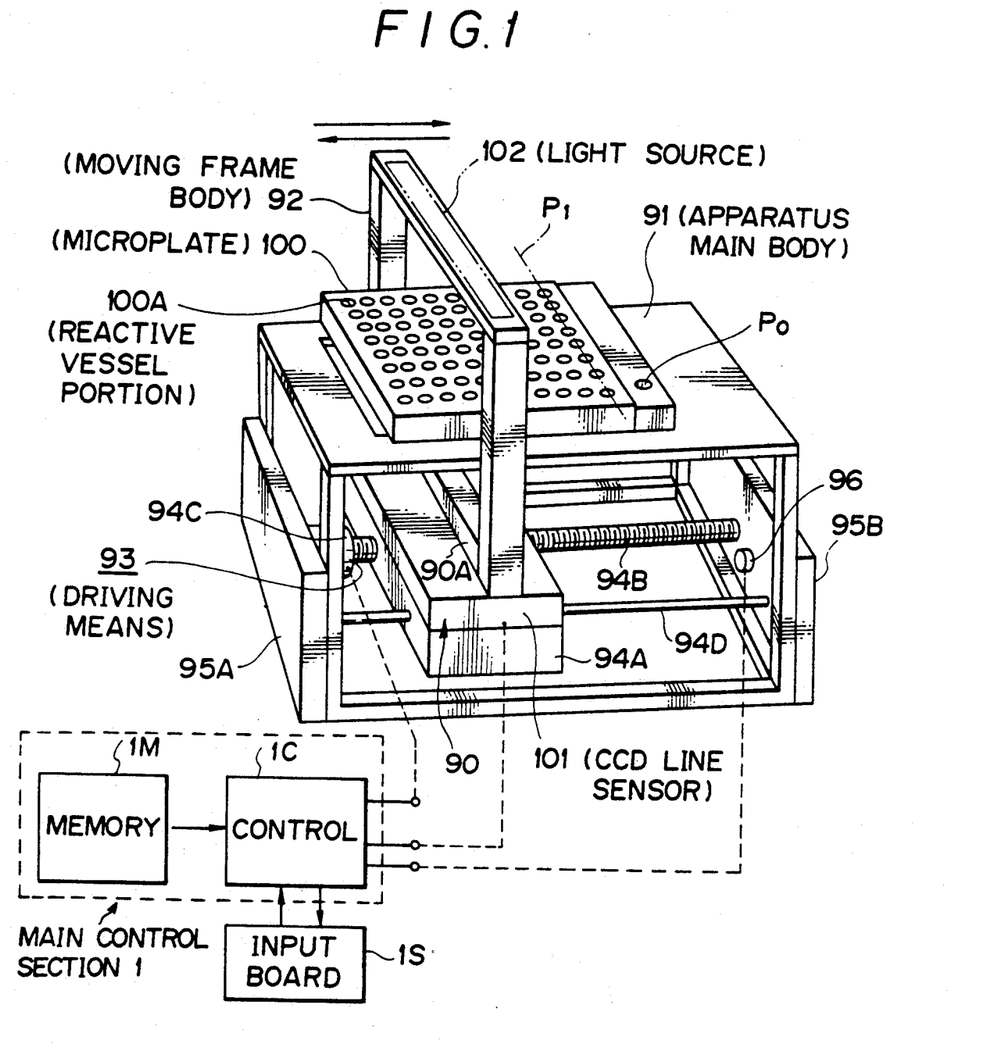
FIG. 1 is a perspective view showing an embodiment of the invention.
Figure 2:
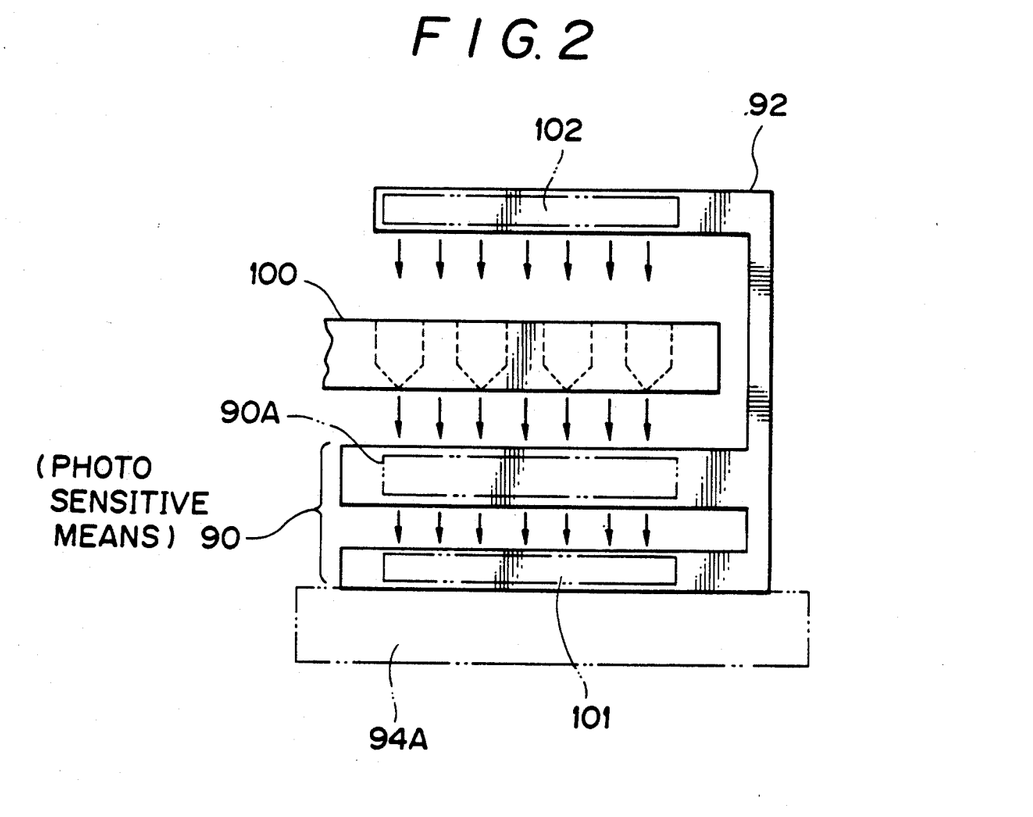
FIG. 2 is an explanatory diagram showing positional relations among a light source section, a line sensor, and an apparatus main body in FIG. 1.
Figure 4:
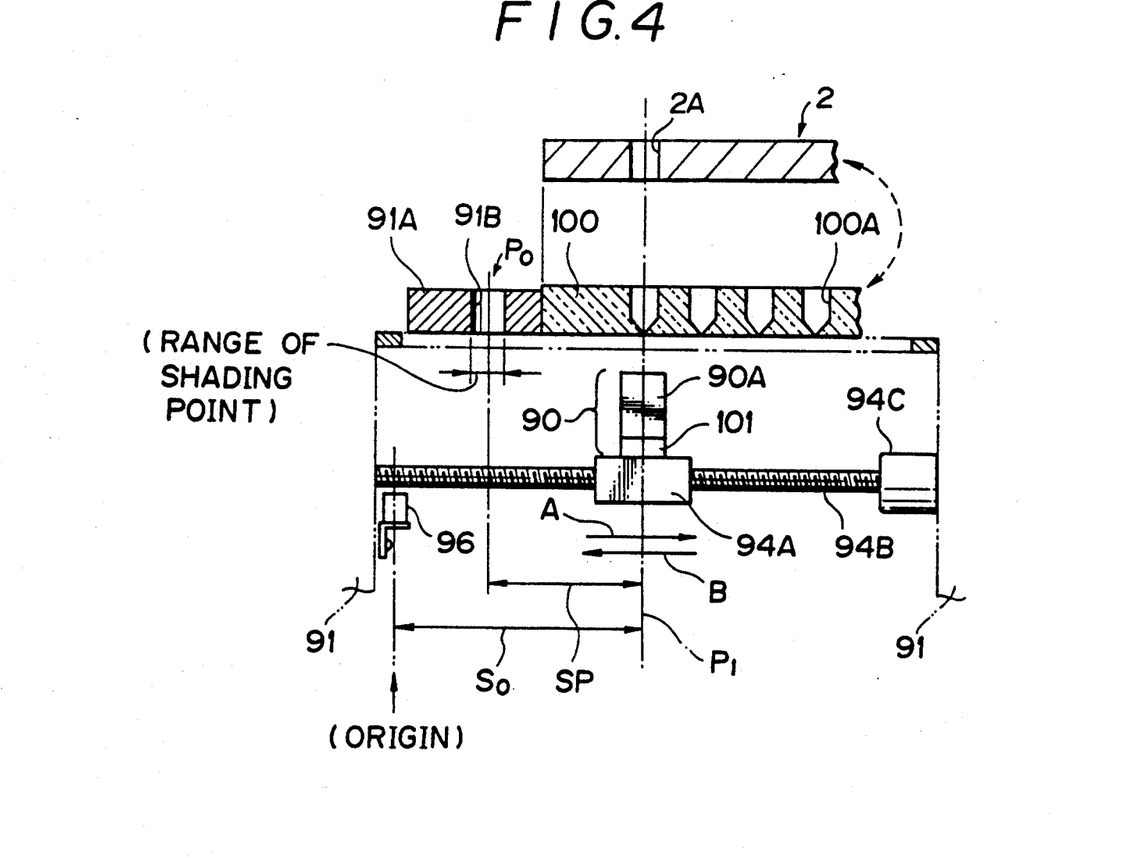
FIG. 4 is an explanatory diagram showing the operation of FIG. 1.

As shown in FIGS. 1 and 4, the driving means 93 comprises: a moving body 94A; a screw mechanism 94B threadedly engaged with the moving body 94A to move the moving body 94A in the directions A and B in the diagrams; a motor 94C with a reduction mechanism to rotate the screw mechanism (preferably a conventional ball screw mechanism) 94B; a guide bar 94D to guide reciprocating movement of the moving body 94A; and attaching plates 95A and 95B secured to main body 91 to support both end portions of the guide bar 94D. One end of a male screw of the screw mechanism 94B is coupled with the motor 94C and the other end is rotatably supported on the attaching plate 95B mentioned above.

The moving frame body 92 and the photosensitive means 90, including the foregoing CCD line sensor 101, are mounted on the moving body 94A. A position sensor 96 is attached on the plate 95B near the other end of the foregoing screw mechanism 94B. The position sensor 96 generates an origin position of the moving body 94A. On the basis of a signal from the position sensor 96, the main control section 1 can recognize when the moving body 94A and moving frame body 92 are located at the origin.

Figure 3:
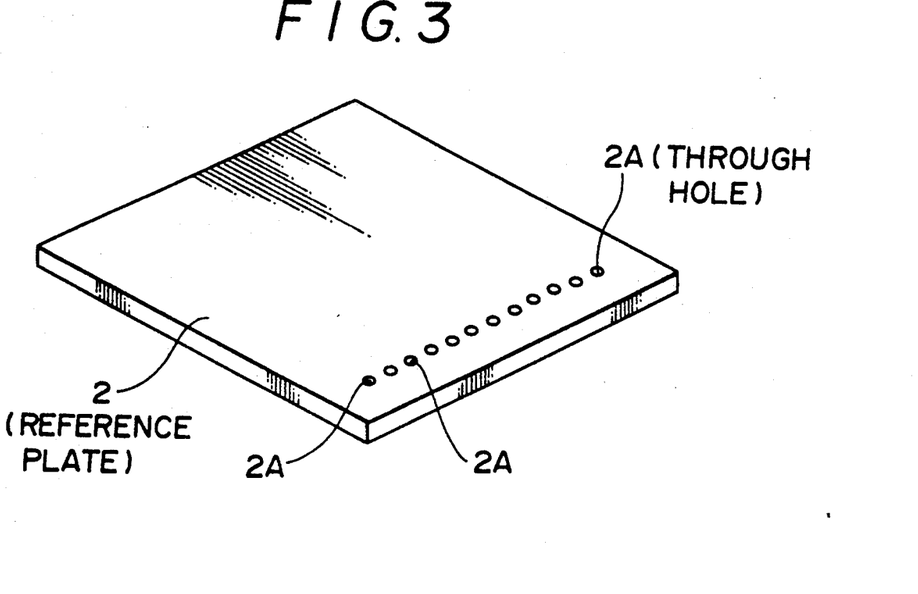
FIG. 3 is a perspective view showing an example of a reference plate which is used as a plate for adjustment of the operation of FIG. 1.

As shown in FIG. 3, the reference plate 2 is the same size as the microplate 100 and has the reference holes 2A at the same relative positions therein as positions $P_1$ (right edge portion in FIG. 1) of the reactive vessels 100A of the first column on the microplate 100. By using the reference plate 2, the positions $P_1$ of the reactive vessels 100A when the microplate 100 is set on the apparatus man body 91 can be stored into the main control section 1 before aggregation pattern detection begins. Reference numerals 1M and 1C respectively denote memory and control blocks provided for the main control section 1. Reference numeral 1S denotes a conventional input board (i.e. I/O board) provided for interfacing with the main control section 1.

Referring to FIG. 4, shading points $P_0$ are defined at predetermined positions located between the microplate 100 and the position sensor 96. The shading points $P_0$ are formed by long through holes 91B formed in a plate-shaped member 91A of apparatus main body 91. The shading points $P_0$ function as optical marks which are used to specify the positions $P_1$ of the reactive vessels 100A of the first column on the microplate 100.

The operation of the embodiment will now be described.

First, at the shipping stage after completion of the checking processes of the product of the whole apparatus, an operation to accurately store the positions $P_1$ of the reactive vessels 100A of the first column on the microplate 100 into the main control section 1 of the apparatus is executed. In this case, the reference plate 2 is first attached to main body 91 at the attaching position of the microplate 100 so as to be in the same position as will ultimately be occupied by the microplate (see FIG. 4). Then, when the signal is supplied to main control section 1 from the position sensor 96, it is confirmed that the moving body 94A is located at the origin position. After completion of such a confirmation, the driving means 93 is made operative and the moving body 94A having the CCD line sensor 101, light source 102, and the like is moved in direction A (FIG. 4). In association with the movement of the moving body 94A, the CCD line sensor 101 first detects transmitted light from the shading points $P_0$. When the moving body 94A further moves, the CCD line sensor 101 then detects the transmitted light from the reference holes 2A of the reference plate 2.

Two different distances $S_0$ (distance from the origin to the first column of the reference holes 2A of the reference plate 2) and SP (distance from the central portion of the shading point $P_0$ to the first column of the reference holes 2A) are measured and stored by the apparatus. In the above measurement, a rotational speed of the motor 94C can be measured and stored by the main control section 1 or also can be accurately measured from the outside by conventional means and, after that, it can also be input from the input board 1S as necessary. For example, the motor speed can be preset to a desired value and controlled by control section 1 to operate at the desired speed. Using a known motor speed, the distances $S_0$ and SP can be measured by control section 1. In this case, the distance SP is actually stored.

The intensities of the transmitted light from the reference holes 2A must be received as the same value because each reference hole 2A is formed in the same shape. Therefore, correction of the position of the CCD line sensor 101, adjustment of the brightness of the light source 102, and the like are also simultaneously executed using the intensities of the transmitted light from the reference holes 2A.

A position of the central portion of each of the reference holes 2A and shading points $P_0$ is specified by detecting the peak of brightness by the main control section 1. In this case, the relation between the peak position of the brightness and the rotational speed of the motor 94C is calculated by using the position of the foregoing position sensor 96 as a reference, and is then stored.

As mentioned above, according to the embodiment, the positions $P_1$ of the reactive vessel portions 100A on the microplate 100 are previously stored into the main control section 1 by using the reference plate 2. Therefore, even if there is a variation of dimensions among the products (for example, variation in dimensions of apparatus main bodies), the CCD line sensor 101 can be immediately moved to the proper photosensitive scanning position on the basis of the distance SP ($S_0$ as necessary) specified for every apparatus main body. Consequently, there is an advantage in that aggregation patterns can be promptly detected, and the reliability of the whole apparatus can be improved.

It should be apparent from the foregoing that the main control section 1 may be implemented using a conventional microprocessor circuit.

Using the disclosed invention, there is no need for the operator to adjust the operating position each time an aggregation pattern is measured. Therefore, aggregation patterns can be promptly measured and the measurement can be automatized and the apparatus provides uniform performance. Thus, an excellent aggregation pattern detecting apparatus which can remarkably improve the reliability of the apparatus and which is not obtained hitherto can be provided.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an aggregation pattern detecting apparatus comprising a microplate having a plurality of reactive vessels in which aggregation patterns are formed, a light source arranged above the microplate, an photosensitive means arranged below the microplate and having a charge coupled device (CCD) line sensor, wherein the improvement comprises:

said microplate being removably fastened to an apparatus main body at a preset position, a moving frame body being movably supported on the apparatus main body for integratedly moving the light source and the photosensitive means in a predetermined direction, driving means for intermittently or continuously moving the moving frame body, control means for controlling the driving means, a reference plate arranged separately from the microplate and having a plurality of through holes corresponding to the reactive vessels on the microplate, the reference plate being removably fastened to said main body at said preset position and means cooperable with said reference plate means for determining a positional relationship between said through holes and a predetermined reference position, thereby establishing a positional relationship between said reaction vessels and said predetermined reference position when said microplate occupies said preset position in lieu of said reference plate means, said control means determining measurement start positions for said reactive vessels based on the positional relationship between said through holes and said predetermined reference position when said microplate means occupies said preset position for measurement purposes.

2. An aggregation pattern detecting apparatus, comprising:

a main body defining thereon a generally upwardly facing support surface;

microplate means removably positionable at a preset position on the support surface of said main body, said microplate means defining therein a plurality of reactive vessels in which aggregation patterns are formed;

a frame body movably supported on said main body for movement generally parallel to said microplate means, said frame body mounting thereon light means and photosensitive means which are movable with the frame body and are vertically spaced so that the light means is disposed above the microplate means and the photosensitive means is disposed below the microplate means;

drive means connected to said frame body for effecting movement thereof;

control means operatively interconnected to the drive means for controlling operation thereof;

reference plate means having a plurality of through holes corresponding to some of the reactive vessels on the microplate means and removably positionable at said preset position on said support surface in lieu of said microplate means;

means cooperable with said reference plate means for determining a positional relationship between said through hole positions and a predetermined reference position, whereby a relationship between said reactive vessels and said predetermined reference position is established;

said control means including memory means for storing the positional relationship between said through holes and said predetermined reference position; and said control means including means for executing predetermined mathematic operations for determining measurement start positions for the reactive vessels on the microplate means based on the stored positional relationship when the microplate means is mounted on the main body for measurement purposes.

3. An aggregation pattern detecting apparatus comprising:

a main body defining thereon a generally upwardly facing support surface;

microplate means removably positionable at a preset position on said support surface, said microplate means defining therein a plurality of reactive vessels in which aggregation patterns are formed;

a light source and a photosensitive means supported on said main body, said microplate means being interposed between said light source and said photosensitive means when positioned in said preset position;

frame means movably supported on said main body for movement generally parallel to said microplate means, said light source and said photosensitive means being mounted on said frame means for movement therewith;

drive means connected to said frame for effecting movement thereof;

reference plate means removably positionable at said preset position on said support surface in place of said microplate means and having a plurality of through holes which correspond to some of said reactive vessels on said microplate means for defining reactive vessel positions which will be occupied by the corresponding reactive vessels when said microplate means occupies said preset position;

means cooperable with said reference plate means for determining a positional relationship between said through hole positions and a predetermined reference position, whereby a relationship between said reactive vessels and said predetermined reference position is established; and means for positioning said frame means relative to said microplate means based on said established positional relationship between said reactive vessel positions and said predetermined reference position.

4. A method for calibrating an aggregation pattern detecting apparatus which includes means defining a generally upwardly facing support surface, microplate means removably positionable at a preset position on said support surface, said microplate means defining therein a plurality of reactive vessels in which aggregation patterns are formed, said microplate means being interposed between a light source and a photosensitive means when positioned in said preset position, a frame supported for movement generally parallel to said microplate means, said light source and said photosensitive means being mounted on said frame for movement therewith, comprising the steps of:

providing a reference plate means having a plurality of through holes which correspond to some of said reactive vessels on said microplate means;

determining that said microplate means is not positioned at said preset position on said support surface;

positioning said reference plate means at said preset position on said support surface; and p1 determining a positional relationship between said through holes and a predetermined reference position while said reference plate means occupies said preset position, thereby establishing a positional relationship that will exist between said reaction vessel positions and said predetermined reference position when said microplate means occupies said preset position.

5. A method according to claim 4, including the steps of removing said reference plate means from said support surface, positioning said microplate means at said preset position on said support surface, and positioning said frame relative to said microplate means based on the previously determined positional relationship between said through holes and said reference position.

6. A method for calibrating an aggregation pattern detecting apparatus which includes means defining a generally upwardly facing support surface, microplate means removably positionable at a preset position on said support surface between a light source and a photosensitive means that comprise optical detecting means, said microplate means defining a plurality of reactive vessels in which aggregation patterns are formed, and means for relatively moving said microplate means and said optical detecting means, comprising the steps of:

providing a reference plate means having a plurality of through holes which correspond to some of said reactive vessels on said microplate means;

determining that said microplate means is not positioned at said preset position on said support surface;

positioning said reference plate means at said preset position on said support surface; and determining a positional relationship between said through hole positions and a predetermined reference position while said reference plate means occupies said preset position, thereby establishing a positional relationship that will exist between said reactive vessel positions and said predetermined reference position when said microplate means occupies said preset position.

* * * * *

UNITED STATES PATENT AND TRADEMARK OFFICE
CERTIFICATE OF CORRECTION

PATENT NO.  :  5 234 665
DATED       :  August 10, 1993
INVENTOR(S) :  Masato Ohta et al It is certified that error appears in the above-identified patent and that said Letters Patent is hereby corrected as shown below:

Column 5, line 41; change "an" to ---and---.
Column 7, lines 38 and 39; delete "p1" and start a
          new paragraph with the word "determining".

Signed and Sealed this

Nineteenth Day of April, 1994

Attest:

BRUCE LEHMAN

Attesting Officer       Commissioner of Patents and Trademarks